United States Patent [19]

Glamkowski et al.

[11] Patent Number: 5,340,936
[45] Date of Patent: Aug. 23, 1994

[54] 8-AZABICYCLO[3.2.1]OCTANE METHANONE AND CORRESPONDING OXIMES

[75] Inventors: Edward J. Glamkowski, Warren, N.J.; David M. Fink, Doylestown, Pa.; Barbara E. Kurys, Elmwood Park; Yulin Chiang, Convent Station, both of N.J.

[73] Assignee: Hoechst-Roussel Pharmaceuticals Inc., Somerville, N.J.

[21] Appl. No.: 37,047

[22] Filed: Mar. 25, 1993

Related U.S. Application Data

[60] Division of Ser. No. 831,027, Feb. 4, 1992, Pat. No. 5,234,931, which is a continuation-in-part of Ser. No. 650,144, Feb. 4, 1991, abandoned.

[51] Int. Cl.$^5$ ............... C07D 451/02; C07D 401/04; C07D 417/04
[52] U.S. Cl. .................... 546/124; 546/126; 546/132
[58] Field of Search ............ 546/126, 132, 124; 514/304

[56] References Cited

U.S. PATENT DOCUMENTS 4,393,069 7/1993 Langbein et al. ............... 514/304

Primary Examiner—Alan L. Rotman
Attorney, Agent, or Firm—Elliott Korsen; Barbara V. Maurer

[57] ABSTRACT

This invention relates to compounds of the formula

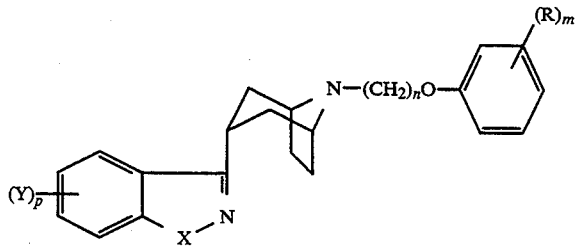

where
X is —O—, —S— or —NH—;
Y is hydrogen, halogen and loweralkoxy;
p is 1 or 2;
n is 2, 3 or 4;
R is hydrogen, loweralkyl, loweralkoxy, hydroxy, halogen, amino, loweralkylamino, nitro, loweralkylthio, trifluoromethoxy, cyano, trifluoromethyl,

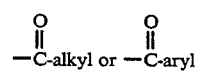

where aryl is

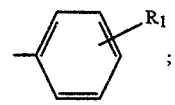

$R_1$ is hydrogen, loweralkyl, loweralkoxy, halogen, hydroxy, carboxyl, loweralkylamino, nitro, loweralkylthio, cyano, and trifluoromethyl;
m is 1 or 2; a pharmaceutically acceptable acid addition salt thereof and, where applicable the geometric and optical isomers and racemic mixtures thereof.

The compounds and compositions of this invention are useful as antipsychotic agent, as 5-HT$_3$ receptor antagonists and as inhibitors of the reuptake of serotonin.

4 Claims, No Drawings

8-AZABICYCLO[3.2.1]OCTANE METHANONE AND CORRESPONDING OXIMES

This is a division, of application Ser. No. 831,027 filed Feb. 4, 1992 now U.S. Pat. No. 5,234,931, which is a continuation-in-part application of U.S. Ser. No. 650,144 filed Feb. 4, 1991, now abandoned.

This invention relates to compounds of the formula

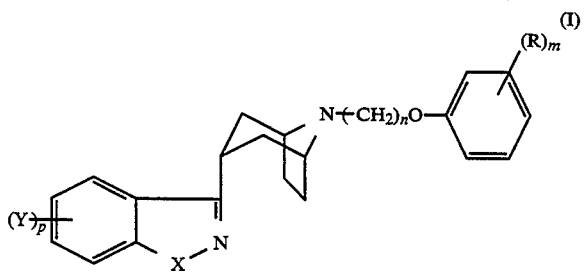

where
X is —O—, —S— or —NH—;
Y is hydrogen, halogen and loweralkoxy;
p is 1 or 2;
n is 2, 3 or 4;
R is hydrogen, loweralkyl, loweralkoxy, hydroxy, halogen, amino, loweralkylamino, nitro, loweralkylthio, trifluoromethoxy, cyano, trifluoromethyl,

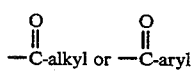

where aryl is;

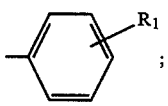

$R_1$ is hydrogen, loweralkyl, loweralkoxy, halogen, hydroxy, carboxyl, loweralkylamino, nitro, loweralkylthio, cyano, and trifluoromethyl;
m is 1 or 2; a pharmaceutically acceptable acid addition salt thereof, and, where applicable the geometric and optical isomers and racemic mixtures thereof.

The compounds and compositions of this invention are useful as antipsychotic agents, as 5-HT$_3$ receptor antagonists and as inhibitors of the reuptake of serotonin.

Subgeneric to the compounds of formula I are compounds of formula II

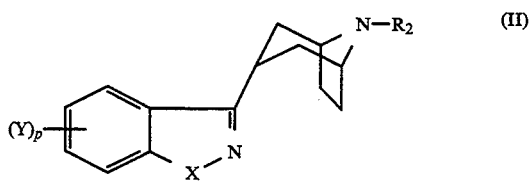

wherein $R_2$ is hydrogen or loweralkyl and X, Y, and p are as previously defined.

This invention also relates to compounds of formula (III)

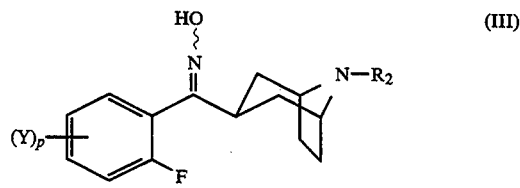

where Y, $R_2$, and p are as defined above, which are useful as intermediates for the preparation of compounds of formula II.

Additionally, this invention relates to compounds of the formula IV

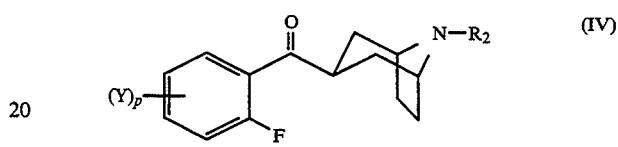

where $R_2$, Y are p are as previously defined which are useful as intermediates for the preparation of compounds of formula II and III.

Preferred embodiments of the invention are those of formula I wherein X is O or S, n is 3 and R is OCH$_3$ and

wherein m=2.

Most preferred embodiments of the invention are those of formula I wherein X is O, n is 3 and R is OCH$_3$ and

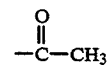

wherein m=2.

Throughout the specification and appended claims, a given chemical formula or name shall encompass all geometric and optical isomers and racemic mixtures where such isomers and mixtures exist, as well as pharmaceutically acceptable acid addition salts thereof and solvates thereof such as hydrate.

In the above definitions, the term "lower" means that the group it is describing contains from 1 to 6 carbon atoms.

The term "alkyl" refers to a straight or branched chain hydrocarbon containing no unsaturation, for example, methyl, ethyl, isopropyl, 2-butyl, neopentyl, n-hexyl, etc.

The term "alkoxy" refers to a monovalent substituent comprising an alkyl group linked through an ether oxygen having its free valence bond from the ether oxygen, e.g. methoxy, ethoxy, propoxy, butoxy, pentoxy, etc.

The term "aryl" means

wherein $R_1$ is hydrogen, loweralkyl, loweralkoxy, hydroxy, halogen, loweralkylamino, nitro, cyano or trifluoromethyl.

The term "loweralkylthio" refers to a monovalent substituent having the formula loweralkyl-S—.

The term "halogen" refers to a member of the halogen family consisting of fluorine, chlorine, bromine and iodine.

The compounds of this invention are prepared in the following manner. The substituents are as defined above unless indicated otherwise.

An aldehyde of the formula

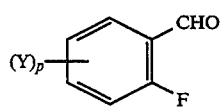

is reacted with an orthoformate in the presence of a catalytic amount of p-toluenesulfonic acid to afford compound (V) of the formula

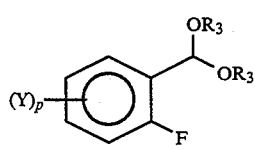

where $R_3$ is loweralkyl. This reaction typically takes place in a loweralkanol solvent such as ethanol, methanol, etc. at a temperature of 0° to 50° C. for 10 to 24 hours.

Compound V is subsequently reacted with a phosphorylating agent such as triethyl phosphite and with boron trifluoride etherate in a suitable solvent such as dichloromethane to afford Compound VI of the formula

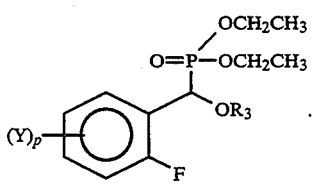

This reaction typically takes place at a temperature of −25° C. to room temperature for 10 to 30 hours.

Compound VI is reacted with n-butyllithium or other suitable agents such as lithium diisopropyl amide and tropinone of the formula

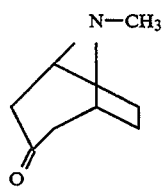

afford Compound VII of the formula

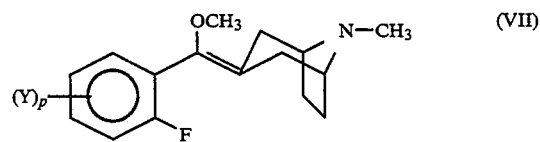

Typically, this reaction takes place in a suitable solvent such as tetrahydrofuran at a temperature of −78° C. to room temperature for 10 to 30 hours.

Compound VII is reacted with aqueous HCl in acetone at reflux for 2 to 8 hours to afford Compound VIII of the invention of the formula

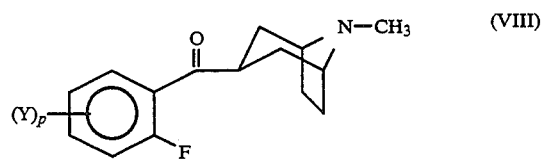

Compound VIII is the intermediate which is generally used for the preparation of the target compounds of this invention.

Preparation of Compounds where X is —O—.

Compounds of the formula

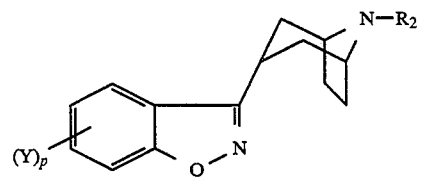

for use in synthesizing the benzisoxazole-substituted compounds of the invention can be prepared as follows.

Compound VIII is reacted with hydroxylamine hydrochloride and ammonium acetate to afford Compound IX of the invention of the formula

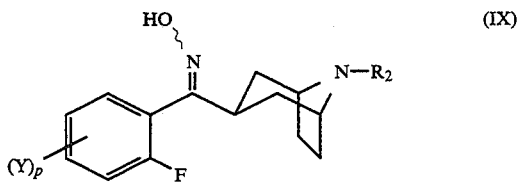

This reaction typically takes place at reflux for 3 to 25 hours in the presence of a solvent such as aqueous ethanol, methanol, etc.

Compound IX is cyclized using a base such as sodium hydroxide or sodium ethoxide heated at reflux to afford Compound X of the invention of the formula

This reaction is conducted in a suitable solvent such as ethanol, methanol etc. for 2 to 10 hours.

Compound X can undergo cleavage of the methyl group by reacting it with vinyl chloroformate or other suitable demethylating agent and then heating to reflux in the presence of a strong acid to afford Compound XI of the invention of the formula

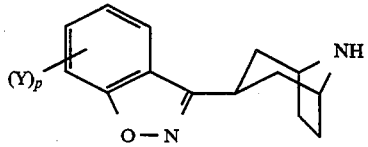
(XI)

The reaction with vinyl chloroformate takes place in a halogenated hydrocarbon solvent such as 1,2-dichloroethane or chloroform for 2 to 10 hours. The reaction with a strong such as HCl also takes place at reflux temperature in a suitable solvent such as ethanol for 1 to 5 hours.

Compound XI is reacted with potassium carbonate and Compound XII of the general formula

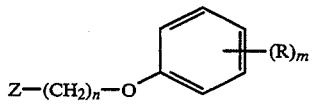
(XII)

where Z is chlorine or bromine and n is 2, 3 or 4 to afford the target benzisoxazoles of the invention of the formula

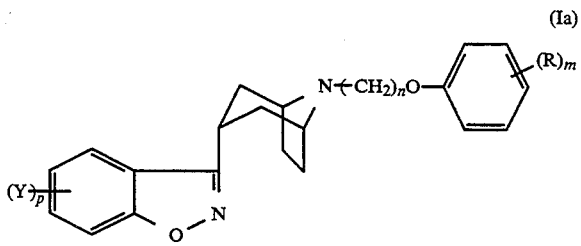
(Ia)

This reaction generally takes place in a suitable solvent such as acetonitrile, dimethylformamide, etc. optionally using a catalytic amount of potassium iodide at reflux for 10 to 30 hours.

Preparation of Compounds Where X is

Compounds of the formula

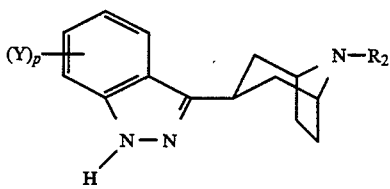

for use in synthesizing the indazolyl-substituted compounds of the invention can be prepared as follows.

Compound VIII is reacted with hydrazine hydrate under standard conditions in a suitable solvent such as ethanol or methanol to afford Compound XIII of the formula

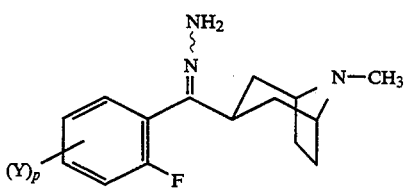
(XIII)

This reaction typically takes place at reflux for 4 to 20 hours.

Compound XIII is cyclized by reacting the hydrazone and potassium carbonate in a suitable solvent such as dimethylformamide to afford Compound XIV of the invention of the formula

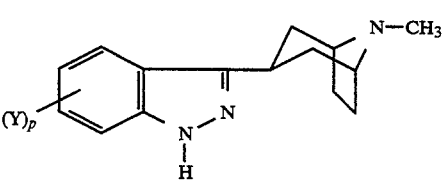
(XIV)

Typically, the reaction is carried out at 90° to reflux for 4 to 20 hours.

Compound XIV is reacted with potassium carbonate and cyanogen bromide to form intermediate XV of the formula

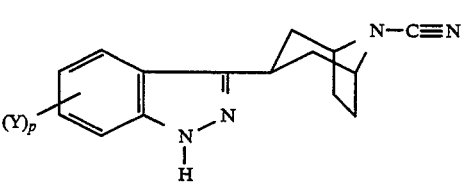
(XV)

This reaction is carried out in a dipolar aprotic solvent such as dimethylformamide or dimethylsulfoxide at ambient temperatures for 2 to 20 hours.

Compound XV is subsequently reduced by means of a metal hydride, e.g., with lithium aluminum hydride to afford Compound XVI of the invention of the formula

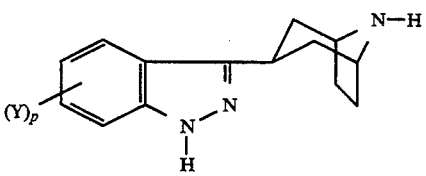
(XVI)

Typically is reaction is conducted in an ethereal solvent such as tetrahydrofuran or diethylether at reflux for 1 to 5 hours.

Compound XVI, the immediate precursor of the target indazoles, is reacted with Compound XII to afford the target indazoles of the invention of the formula

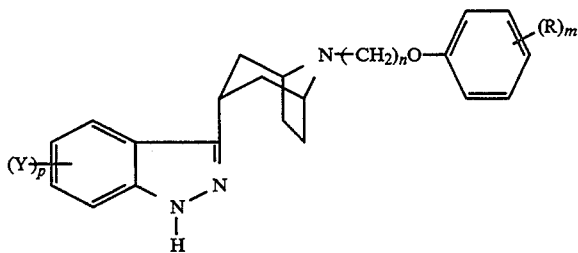

This reaction takes place under essentially the same conditions as the synthesis of the benzisoxazole substituted target compounds of the invention.

Preparation of Compounds Where X is —S—.

Compounds of the formula

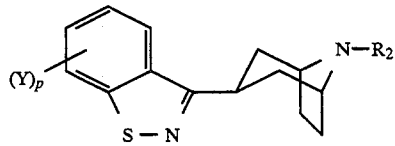

For use in the synthesis of benzisothiazolyl compounds of the invention can be prepared as follows.

Compound VIII is reacted with sulphur in a solution of ammonia in a solvent such as 2-methoxyethanol to afford Compound XVII of the invention of the formula

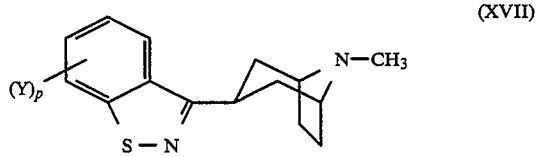
(XVII)

typically, this reaction takes place at a temperature of about 100° to 180° C. for 2 to 5 hours.

Compound XVII is subsequently reacted with vinyl chloroformate and potassium carbonate at reflux in a suitable solvent such as dichloroethane for 2 to 10 hours and the resultant product is further reacted with HCl in ethanol at reflux in a standard cleavage reaction to form Compound XVIII of the invention of the formula

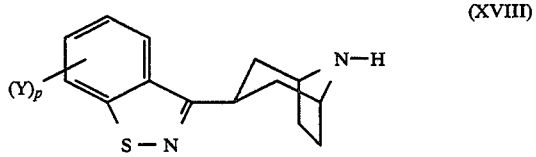
(XVIII)

Compound XVIII, the immediate precursor of the target benzisothiazoles is alkylated in a manner similar to the alkylation of the other target compounds of the invention.

The compounds of the present invention are useful for treating psychoses by virtue of their ability to elicit an antipsychotic response in animals. Antipsychotic activity is determined in the climbing mice assay by a method similar to to those described by P. Protais, et al., Psychopharmacol., 50:1 (1976) and B. Costall, Eur. J. Pharmacol., 50:39 (1978):

Subject CK-1 male mice (23-27 grams) are grouped-housed under standard laboratory conditions. The mice are individually placed in wire mesh stick cages (4"×10") and are allowed one hour for adaption and exploration of the new environment. Then apomorphine is injected subcutaneously at 1.5 mg/kg, a dose causing climbing in all subjects for 30 minutes. Compounds to be tested for antipsychotic activity are injected intraperitoneally or given oral doses at various time intervals, e.g. 30 minutes, 60 minutes, etc. prior to the apomorphine challenge at a screening dose of 10–60 mg/kg.

For evaluation of climbing, 3 readings are taken at 10, 20 and 30 minutes after apomorphine administration according to the following scale:

| Climbing Behavior Mice with: | Score |
|---|---|
| 4 paws on bottom (no climbing) | 0 |
| 2 paws on the wall (rearing) | 1 |
| 4 paws on the wall (full climb) | 2 |

Mice consistently climbing before the injection of apomorphine are discarded.

With fully-developed apomorphine climbing, the animals are hanging on to the cage walls, rather motionless, over longer periods of time. By contrast, climbs due to mere motor stimulation usually only last a few seconds.

The climbing scores are individually totaled (maximal score: 6 per mouse over 3 readings) and the total score of the control group (vehicle intraperitoneally-apomorphine subcutaneoulsy) is set to 100%. $ED_{50}$ values with 95% confidence limits, calculated by a linear regression analysis, of representative compounds of the present invention as well as a standard antipsychotic agent are presented in Table 1.

TABLE 1

| COMPOUND | CLIMBING MOUSE ASSAY ($ED_{50}$ mg/kg, ip) |
|---|---|
| [4-[3-[6-Fluoro-1,2-benzisoxazol-3-yl]-8-azabicyclo[3.2.1]octan-8-yl]-propoxy]-3-methoxyphenyl]ethanone monohydrochloride | 5.0 |
| [4-[3-[3-[6-Fluoro-1,2-benzisoxazol-3-yl]-8-azabicyclo[3.2.1]octan-8-yl]-ethoxy]-3-methoxyphenyl]ethanone fumarate | 12.5 |
| Clozapine (reference) | 8.1 |

Antipsychotic activity can also be predicted by virtue of the affinity of these compounds for the 5-HT$_3$ binding site in the brain. Compounds which function as 5-HT$_3$ antagonists are believed to be useful in the treatment of schizophrenia.

$^3$H-GR 65630 Binding to Rat Entorhinal Cortex Membranes

5-HT$_3$ Receptor Binding Assay

The purpose of this assay is to determine the affinity of test compounds for the binding site in the brain. This assay may be useful for predicting the potential of compounds to exhibit antipsychotic profiles.

Presently, it is generally accepted that there are three different receptor subtypes the neurotransmitter serotonin (5-HT); 5-HT$_1$, 5-HT$_2$ and 5-HT$_3$. The 5-HT$_1$ and 5-HT$_2$ binding sites have been well characterized and further subdivided based on data from binding and functional activity studies. The 5-HT$_3$ binding site, on the other hand, has only recently begun to be characterized. Originally, it was believed that 5-HT$_3$ binding sites existed only in the periphery. However, with the recent introduction of potent selective 5-HT$_3$ antagonist drugs such as GR65630, zacopride, ICS 205 930 and MDL 2222, data from binding studies have indicated that 5-HT$_3$ binding sites have been detected in limbic and dopamine containing brain areas (entorhinal cortex, amygdala, nucleus accumbens and tuberculum olfactorium). Besides possessing selective binding in dopamine rich areas, 5-HT$_3$ antagonists have been reported to block behavioral effects associated with certain drugs of abuse (nicotine and morphine) and to be active in behavioral tests predictive of anxiolytic activity. Based on these selective regional binding results and behavioral studies, it has been speculated that 5-HT$_3$ antagonists may have a therapeutic benefit in disease states believed to be associated with excessive dopaminergic activity; i.e., schizophrenia, anxiety and drug abuse.

Procedure

A. Regents
1. 0.05M Krebs-Hepes buffer, pH 7.4
   11.92 g Hepes
   10.52 g NaCl
   0.373 g KCl
   0.277 g CaCl$_2$
   0.244 g MgCl$_2$6H$_2$O
   bring to 1 liter with distilled H$_2$O
   bring pH up to 7.4 (at 4° C.) with 5N NaOH 2. For IC$_{50}$ determinations: [$^3$H]-GR65630 is made up to a concentration of 1.0 nM in Krebs-Hepes buffer such that when 100 µl assay is added to each tube a final concentration of 0.4 nM is attained in the 250 µl assay.
3. Zacopride maleate is made up to a concentration of 500 µM in Krebs-Hepes buffer. 50 µl is added to each of 3 tubes for the determination of nonspecific binding (yields a final concentration of 100 µM in the 250 µl assay).
4. Test Compounds. For most assays, a 50 µM stock solution is made up in a suitable solvent and serially diluted with Krebs-Hepes buffer such that when 50 µl of drug is combined with the total 250 µl assay, a final concentration from $10^{-5}$ to $10^{-8}$ M is attained. Characteristically seven concentrations are studied for each assay; however, higher or lower concentrations may be used, depending on the potency of the drug.

B. Tissue Preparation

Male Wistar rats ( 150–200 g) are decapitated, the entorhinal cortex removed, weighed and homogenized in 10 volumes of ice-cold 0.05M Krebs-Hepes buffer, pH 7.4. The homogenate is centrifuged at 48,000 g for 15 minutes at 4° C. The resulting pellet is rehomogenized in fresh Krebs-Hepes buffer and recentrifuged at 48,000 g for 15 minutes at 4° C. The final pellet is resuspended in the original volume of ice-cold Krebs-Hepes buffer. This yields a final tissue concentration of 1.2–1.6 mg/ml with the addition of 100 µl to the assay. Specific binding is approximately 55–65% of total bound ligand.

C. Assay

100 µl Tissue suspension
100 µl [$^3$H]-GR65630
50 µl Vehicle (for total binding) or 500 µM Zacopride maleate (for nonspecific binding) or appropriate drug concentration Sample tubes are kept on ice for additions, then vortexed and incubated with continuous shaking for 30 minutes at 37° C. At the end of incubation period, the incubate is diluted with 5 ml of ice-cold Krebs-Hepes buffer and immediately vacuum filtered through Whatman GF/B filters, followed by two 5-ml washes with ice-cold Krebs-Hepes buffer. The filters are dried and counted in 10 ml of liquid scintillation cocktail. Specific GR65630 binding is defined as the difference between the total binding and that bound in the presence of 100 µM Zacopride. IC$_{50}$ calculations are performed using computer-derived log-probit analysis.

The results of this assay for representative compounds of this invention as well as reference compounds are presented in Table 2.

TABLE 2

| COMPOUND | IC$_{50}$ (µM) |
| --- | --- |
| 3-(1,2-Benzisoxazol-3-yl-8-azabicyclo[3.2.1]-octane hydrochloride | 1.17 |
| 3-(6-Fluoro-1,2-benzisoxazol-3-yl)-8-azabicyclo-[3.2.1]octane hydrochloride | 0.059 |
| 3-(1H-Indazol-3-yl)-8-methyl-8-azabicyclo-[3.2.1]octane | 3.3 |
| 3-[1,2-Benzisothiazol-3-yl]-8-methyl-8-azabicyclo[3.2.1]octane hydrochloride | 2.6 |
| [4-[3-[3-[6-Fluoro-1,2-benzisothiazol-3-yl]-8-azabicyclo[3.2.1]octan-8-yl]propoxy]-3-methoxyphenyl] ethanone | 2.68 |
| 3-[6-Fluoro-1,2-benzisothiazol-3-yl]-8-azabicyclo[3.2.1]octane fumarate | 0.34 |
| 3-(1H-Indazol-3-yl)-8-azabicyclo[3.2.1]-octane fumarate hemihydrate | 2.15 |
| 3-(6-Fluoro-1H-indazol-3-yl)-8-azabicyclo[3.2.1]-octane hydrochloride | 2.26 |
| MDL 72222 (Reference) | 0.532 |
| Ondansetron (Reference) | 0.089 |

Antipsychotic response is achieved when the compounds of the present invention are administered to a subject requiting such treatment as an effective oral, parenteral, or intravenous dose of from 0.01 to 50 mg/kg of body weight per day. It is to be understood, however, that for any particular subject, specific dosage regimens should be adjusted according to the individual need and the professional judgment of the person administering or supervising the administration of the aforesaid compound. It is to be further understood that the dosages set forth herein are exemplary only and they do not, to any extent, limit the scope or practice of the invention.

The compounds of the present invention may also be useful for the treatment of depression and/or obsessive-compulsive disorder by virtue of their ability to inhibit the reuptake of serotonin.

Some researchers have suggested that subjects with serotonergic hypofunction comprise a biochemical subgroup of depressed patients. Others claim that altered serotonergic function determines the change associated with obsessive-compulsive disorder.

This activity is determined in an assay which measures $^3$H-serotonin uptake in rat whole brain and hypothalamic synaptosomes. The assay described below is used as a biochemical screen for potential antidepressants which block serotonin [5-hydroxytryptamine [5HT]) uptake.

$^3$H]-5HT transport has been characterized in the central nervous system tissue and found to be saturable, sodium and temperature-dependent, inhibited by ouabain, metabolic inhibitors, tryptamine analogs and tricyclic antidepressants.

Procedure

A. Animals
   Male CR Wistar rats
B. Reagents
   1. Krebs-Henseleit Bicarbonate Buffer, pH 7.4 (KHBB):
      Prepare a 1 liter batch containing the following salts.

|  | grams/l | mM |
|---|---|---|
| NaCl | 6.92 | 118.4 |
| KCl | 0.35 | 4.7 |
| $MgSO_4.7H_2O$ | 0.29 | 1.2 |
| $KH_2PO_4$ | 0.16 | 2.2 |
| $NaHCO_3$ | 2.10 | 24.9 |
| $CaCl_2$ | 0.14 | 1.3 |
| Prior to use add: | | |
| Dextrose | 2 mg/ml | 11.1 |
| Iproniazid phosphate | 0.30 mg/ml | 0.1 |

The batch is aerated for 60 minutes with 95% $O_2$/5% $CO_2$, the pH is checked to insure it is at 7.4±0.1.

2. Add 0.32M sucrose: 21.9 g of sucrose, q.s. to 200 ml.
3. A 0.1 mM stock solution of serotonin creatinine $SO_4$ is made up in 0.01N HCl. This is used to dilute the specific activity of the radiolabeled 5HT.
4. 5-[1,2-$^3$H(N)]-Hydroxytryptamine creatinine sulfate (serotonin) specific activity 20–30 Ci/mmol is used.

The final desired concentration of $^3$H-5HT in the assay is 50 nM. The dilution factor is 0.8. The KHBB is made up to contain 62.5 nM of [$^3$H]-5HT.
Add to 100 ml of KHBB.

| A) | 56.1 µl of 0.1 mM 5HT = | 56.1 nM |
|---|---|---|
| B) | 0.64 nmol of $^3$H-5HT = | 6.4 nM |
|  |  | 62.5 nM |

5. For most assays, a 1 mM stock solution of the test compound is made up in a suitable solvent and serially diluted such that the final concentration in the assay ranges from $2 \times 10^{-8}$ to $2 \times 10^{-5}$M. Seven concentrations are used for each assay.

C. TISSUE PREPARATION

Male Wistar rats are decapitated and the brain rapidly removed. Either whole brain minus cerebella or hypothalmus is weighed and homogenized in 9 volumes of ice-cold 0.32M sucrose using a Potter-Elvejhem homogenizer, The homogenate is centrifuged at 1000 g for 10 minutes at 0°–4° C. The supernatant ($S_1$) is decanted and is used for uptake determination.

D. ASSAY

800 µl KHBB+[$^3$H]-5HT
20 µl Vehicle or appropriate drug
200 µl Tissue suspension concentration Tubes are incubated at 37° C. under a 95% $O_2$/5% $CO_2$ atmosphere for 5 minutes. For each assay, 3 robes are incubated with 20 µl of vehicle at 0° C. in an ice bath. After incubation all tubes are immediately centrifuged at 4000 g for 10 minutes. The supernatant fluid is aspirated and the pellets dissolved by adding 1 ml of solubilizer (Triton X-100 and 50% ethanol, 1:4 v/v). The robes are vigorously vortexted, decanted scintillation vials, and counted in 10 ml of Liquiscint scintillation counting cocktail. Active uptake is the difference between cpm at 37° C. and 0° C. The per cent inhibition at drug concentration is the mean of three determinations. $IC_{50}$ values are derived from log-probit analysis.

The results of this assay for representative compounds of this invention as well as reference compounds are presented in Table 3.

TABLE 3

| COMPOUND | 5-HT-$IC_{50}$ (µM) |
|---|---|
| [4-[2-[3-[1,2-Benzisoxazol-3-yl]-8-azabicyclo[3.2.1]octan-8-yl]-ethoxy]-3-methoxyphenyl]ethanone fumarate | 0.01 |
| [4-[4-[3-[1H-Indazol-3-yl]-8-azabicyclo-[3.2.1]octan-8-yl]butoxy]-3-methoxyphenyl]-ethanone fumarate hemihydrate | 0.07 |
| [4-[4-[3-[6-Fluoro-1H-indazol-3-yl]-8-azabicyclo[3.2.1]-octan-8-yl]butoxy]-3-methoxyphenyl]ethanone | 0.02 |
| [4-[4-[3-[1,2-Benzisothiazol-3-yl]-8 azabicyclo[3.2.1]octan-8-yl]-butoxy]-3-methoxyphenyl]ethanone monohydrochloride | 0.027 |
| Chloripramine (reference) | 0.15 |
| Fluoxetine (reference) | 0.247 |

Antidepressive response is achieved when the compounds of the present invention are administered to a subject requiring such treatment as an effective oral, parenteral, or intravenous dose of from 1 to 100 mg/kg of body weight per day. It is to be understood, however, that for any particular subject, specific dosage regimens should be adjusted according to the individual need and the professional judgment of the person administering or supervising the administration of the aforesaid compound. It is to be further understood that the dosages set forth herein are exemplary only and they do not, to extent, limit the scope or practice of the invention.

Effective quantifies of the compounds of the present invention may be administered to a subject by any one of various methods, for example, orally as in capsules or tablets, parenterally in the form of sterile solutions or suspensions, and in some cases intravenously in the form of sterile solutions.

The compounds of the present invention, while effective themselves, may be formulated and administered in the form of their pharmaceutically acceptable acid addition salts for purposes of stability, convenience of crystallization, increased solubility and the like.

Preferred pharmaceutically acceptable addition salts include salts of inorganic acids such as hydrochloric, hydrobromic, sulfuric, nitric, phosphoric and perchloric acids; as well as organic acids such as tartaric, citric, acetic, succinic, maleic, fumaric, and oxalic acids.

The active compounds of the present invention may be administered orally, for example, with an inert diluent or with an edible carder. They may be enclosed in gelatin capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 0.5% of active compound, but may be varied depending upon the particular form and may conveniently be between 4% to about 75% of the weight of the unit. The amount of compound present in such composition is such that a suitable dosage will be obtained. Preferred compositions and preparations according to the present invention are prepared so that an oral dosage unit form contains between 1.0–300 mgs of active compound.

The tablets, pills, capsules, troches and the like may also contain the following ingredients: a binder such as microcrystalline cellulose, gum tragacanth or gelatin; an excipient such as starch or lactose, a disintegrating agent such as alginic acid, Primogel ™, corn starch and the like; a lubricant such as magnesium stearate or Sterotex ®; a glidant such as colloidal silicon dioxide; and a sweetening agent such as sucrose or saccharin or a flavoring agent such as peppermint, methyl salicylate, or orange flavoring may be added. When the dosage unit form is a capsule, it may contain, in addition to materials of the above type, a liquid carrier such as fatty oil. Other dosage unit forms may contain other various materials which modify the physical form of the dosage unit, for example, as coatings. Thus tablets or pills may be coated with sugar, shellac, or other enteric coating agents. A syrup may Contain, in addition to the active compounds, sucrose as a sweetening agent and certain preservatives, dyes and colorings and flavors. Materials used in preparing these various compositions should be pharmaceutically pure and non-toxic in the amounts used.

For the purpose of parenteral therapeutic administration, the active compounds of the invention may be incorporated into a solution or suspension. These preparations should contain at least 0.1% of the aforesaid compound, but may be varied between 0.5 and about 30% of the weight thereof. The amount of active compound in such compositions is such that a suitable dosage will be obtained. Preferred compositions and preparations according to the present invention are prepared so that a parenteral dosage unit contains between 0.5 to 100 mgs of active compound.

The solutions or suspensions may also include the following components; a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

Following are typical examples of compounds of the invention that can be prepared by following the methods of preparation described earlier:

[4-[2-[3-[6-fluoro-1,2-benzisothiazol-3-yl]-8-azabicyclo[3.2.1]octan-8-yl]propoxy]-3-methoxyphenyl]ethanone;

[4-[2-[3-[6-fluoro-1,2-benzisoxazol-3-yl]-8-azabicyclo[3.2.1]octan-8-yl]propoxy]-2-methylphenyl]ethanone;

[4-[2-[3-[6-fluoro-1,2-benzisoxazol-3-yl]-8- azabicyclo[3.2.1]octan-8-yl]propoxy]-2- methoxyphenyl ethanone;

[4-[2-[3-[6-fluoro-1,2-benzisoxazol-3-yl]-8-azabicyclo[3.2.1]octan-8-yl]propoxy]-3-methylaminophenyl]ethanone;

N-[4-[2-[3-[6-fluoro-1,2-benzisoxazol-3-yl]-8-azabicyclo[3.2.1]octan-8-yl]propoxy]-3-methoxyphenyl]acetamide;

[4-[2-[3-[6-chloro-1,2-benzisoxazol-3-yl]-8-azabicyclo[3.2.1]octan-8-yl]propoxy]-3-methoxyphenyl]ethanone;

[4-[2-[3-[6-fluoro-1,2-benzisoxazol-3-yl]-8-azabicyclo[3.2.1]octan-8-yl]propoxy]-3-methoxybenzonitrile;

[4-[2-[3-[6-fluoro-1,2-benzisoxazol-3-yl]-8-azabicyclo[3.2.1]octan-8-yl]propoxy]-3-bromophenyl]ethanone;

[4-[2-[3-fluoro-1,2-benzisoxazol-3-yl]-8-azabicyclo[3.2.1]octan-8-yl]3methylmercaptophenyl]ethanone;

[4-[2-[3-[6-fluoro-1,2-benzisothiazol-8-azabicyclo[3.2.1]octan-8-yl]butoxy]-3-methoxyphenyl]ethanone;

[4-[2-[3-[6-fluoro-1,2-benzisothiazol-3-yl]-8-azabicyclo[3.2.1]octan-8-yl]-3methoxyphenyl]ethanone; and

[4-[2-[3-[6-fluoro-1,2-benzisoxazol-3-yl]-8-azabicyclo[3.2.1]octan-8-yl]propoxyl]phenyl]ethanone.

The following examples are for illustrative purposes only and are not to be construed as limiting the invention. All temperatures are given in degrees centrigrade (°C.) unless indicated otherwise.

EXAMPLE 1 a. Diethyl-1-(2-fluorophenyl)-1-methoxymethane phosphonate

A solution of 2-fluorobenzaldehyde (50 g), trimethyl orthoformate (400 ml) in methanol (11) and a catalytic amount of p-toluenesulfonic acid was stirred at room temperature for 21 hours. Sodium carbonate (20 g) was added and the mixture was stirred for 10 minutes. The solids were filtered, and the solution was concentrated to an oil. The oil was extracted with ether (300 ml), and filtered again. Removal of ether left 65 g of dimethyl acetal as an oil. Boron trifluoride etherate (55 g) was added dropwise to the solution of the acetal and triethyl phosphite (67 g) in dichloromethane (DCM) (800 ml) at −25° C. (CCl4/dry ice). The resulting solution was stirred at ambient temperature for 16 hours. The DCM solution was washed with water, brine, dried over MgSO4, filtered and concentrated to yield an oil (111 g). Purification by flash chromatography on silica gel hexane/ethyl acetate/methanol) yielded 90 of an oil. A sample (6.23 g) was further purified by vacuum distillation (collected at 140°–145° C.) to provide 5.2 g of diethyl-1-(2-fluorophenyl)-1-methoxymethane phosphonate.

Analysis: Calculated for $C_{12}H_{18}FO_4P$: 52.18% C 6.57% H Found: 51.77% C 6.57% H b. (2-Fluorophenyl)(8-methyl-8-azabicyclo[3.2.1]-octan-3-yl)methanone hydrochloride Diethyl-1-(2-fluorophenyl)-1-methoxymethane phosphonate (25 g) in tetrahydrofuran (THF) (400 ml) was treated with n-butyl lithium (37 ml, 2.5M in hexane) slowly at −78° C. under nitrogen. The mixture was stirred for 1 hour, then a solution of tropinone (12.4 g) in THF (40 ml) was added slowly at low temperature. The reaction was stirred overnight at room temperature and then water (300 ml) was added. The organics were extracted into ethyl acetate. The ethyl acetate solution was washed with brine and dried over MgSO4, filtered and concentrated to yield an oil (27.2 g). This oil was refluxed in a solution of acetone (500 ml) and 6N HCl (150 ml) for 6 hours. Acetone was removed on a rotary evaporator and the aqueous solution was extracted once with ethyl acetate (100 ml), then basified with $K_2CO_3$ to pH 8. The product was extracted with DCM (600 ml) and this solution was washed with brine and dried over MgSO4 to yield 15.2 g of crude solid. The crude solid was purified by flash chromatography over silica gel (10% CH$_3$OH:90% ethyl acetate/0.5% diethylamine) to yield 14 gm of a solid. This material was purified further by treatment of 2.5 g of free base with HCl in ethanol. The salt obtained was recrystallized twice from ethanol to yield 1.33 g, m.p. 231°-232° C.

Analysis: Calculated for C$_{15}$H$_{19}$ClFNO: 63.49% C 6.75% H 4.94% N Found: 63.57% C 6.67% H 4.85% N Z-(2-Fluorophenyl)(8-methyl-8-azabicyclo[3.2.1]octan-3-yl)methanone oxime hydrochloride A mixture of (2-fluorophenyl)(8-methyl-8-azabicyclo[3.2.1]octan-3-yl)methanone (29.5 g), hydroxylamine hydrochloride (16.5 g) and ammonium acetate (27.5 g) were heated in 80 ml of refluxing ethanol-water (3:1 mixture) for 19 hours. The mixture was cooled and the precipitated product was collected (25.2 g).

d. 3-(1,2-Benzisoxazol-3-yl)-8-methyl-8azabicyclo[3.2.1]octane hydrochloride monohydrate A solution of (2-fluorophenyl)(8-methyl-8-azabicyclo[3.2.1]octan-3-yl)methanone oxime (14 g) in 56 ml of 10% sodium hydroxide solution and 140 ml of ethanol was heated at reflux for 4 hours. The resulting solution was cooled, diluted with water, and the product was extracted into dichloromethane. The combined organic layers were washed with brine, dried over magnesium sulfate, filtered, and concentrated to provide 13.1 g of an oil. The crude product was dissolved in methanol and acidified. The volume of solvent was reduced, ethyl acetate was added, and the product crystallized from solution. The product was collected by filtration, affording 5.5 g of 3-(1,2-benzisoxazol-3-yl)-8-methyl-8-azabicyclo[octane hydrochloride monohydrate, as crystals, m.p. 232°-233° C.

Analysis Calculated for C$_{15}$H$_{21}$ClN$_2$O$_2$: 60.70% C 7.13% H 9.44% N Found: 60.83% C 6.78% H 9.42% N e. 3-(1,2-Benzisoxazol-3-yl)-8-azabicyclo[3.2.1]octane hydrochloride Vinyl chloroformate (3.6 g) was added dropwise to a solution of 3-(1,2-benzisoxazol-3-yl)-8-methyl-8-azabicyclo[3.2.1]octane (6.0 g) in 125 ml of 1,2-dichloroethane at 0° C. The resulting suspension was heated at reflux for 3 hours, the solution was cooled, and the solvent was removed in vacuo. The residue was suspended in 125 ml of ethanol and acidified with HCl in isopropanol (to about a pH of 1), and the mixture was heated at reflux for 2 hours. The mixture was cooled, and 3.9 g of 3-(1,2-benzisoxazol-3-yl)-8-azabicyclo[3.2.1]octane hydrochloride crystallized, m.p. 264°-268° C.

Analysis:

Calculated for C$_{14}$H$_{17}$ClN$_2$O: 63.51% C 6.47% H 10.58% N Found: 63.67% C 6.51% H 10.42% N f. [4-[4-[3-[1,2-Benzisoxazol-3-yl]-8-azabicyclo[3.2.1]octan-8-yl]butoxy]-3-methoxyphenyl]ethanone hydrochloride A mixture of 3-(1,2-benzisoxazol-3-yl)-8-azabicyclo[3.2.1]octane (3.7 g), 4-(4-bromobutoxy)-3-methoxyphenyl ethanone (5.3 g), and potassium carbonate (4.5 g) was heated in 65 ml of refluxing acetonitrile for 22 hours. The resulting mixture was allowed to cool to room temperature and then filtered. The filtrate was diluted with dichloromethane, and then washed sequentially with water and brine, dried over K$_2$CO$_3$, filtered, and concentrated to provide 7.1 g of crude product. Purification by HPLC on silica gel (elution with ethyl acetate) afforded 4.6 g of product as an oil. The oil was dissolved in hot ethanol and treated with a solution of HCl in isopropanol. Isopropyl ether was added to the solution, and the hydrochloride was allowed to crystallize. Filtration gave 4.48 g of [4-[4-[3-[1,2-benzisoxazol-3-yl]-8-azabicyclo[3.2.1]octan-8-yl]butoxy]-3-methoxyphenyl]ethanone hydrochloride, m.p. 216.5°-218° C.

Analysis: Calculated for C$_{27}$H$_{33}$ClN$_2$O$_4$: 66.86% C 6.86% H 5.78% N Found: 66.78% C 7.11% H 5.53% N

EXAMPLE 2 a. Diethyl-1-(2,4-difluorophenyl )-1-methoxymethane phosphonate

Boron trifluoride etherate (56 ml) was added dropwise to a solution of 2,4-difluorobenzaldehyde dimethyl acetal (79 g) and triethylphosphite (73.5 g) in DCM (1 l) at −25° C. The mixture was stirred at ambient temperature for 16 hours. The organic solution was washed with H$_2$ and brine and dried over MgSO$_4$. The solvent was removed to leave an oil (∼160 g). Purification by flash chromatography on silica gel column (elution with 40% heptane: 60% DCM, with DCM, followed by ethyl acetate: DCM) provided 107 g of an oil.

Analysis: Calculated for C$_{12}$H$_{17}$F$_2$O$_4$P: 48.99% C 5.82% H Found: 48.11% C 5.94% H b. (2,4-Difluorophenyl)(8-methyl-8-azabicyclo[3.2.1]octan-3-yl)methanone hydrochloride Diethyl-1-(2,4-difluorophenyl))-1-methoxymethane phosphonate (76 g) was dissolved in THF (1600 ml). The solution was cooled to −78° C. and n-BuLi (103.4 ml of a 2.5M solution in hexanes) was added dropwise at a rate such that the temperature never rose above −65° C. The resulting solution was stirred for 1 hour. Tropinone (32.7 g) dissolved in THF (100 ml) was then added slowly dropwise to the reaction mixture. After complete addition, the mixture was allowed to warm slowly to room temperature and was stirred overnight. A saturated NaCl solution (1.5 L) was added to the reaction mixture. The layers were separated and the organic layer was collected and dried over MgSO$_4$. The solvent was removed via rotary evaporation to yield an oil (73 g). This oil (38 g) was dissolved in acetone (2L). Water (350 ml) and concentrated HCl (182 ml) were added slowly and the mixture was refluxed for 3 hours. The acetone was removed via rotary evaporation. The aqueous residue which remained was extracted with ethyl acetate, basified with K$_2$CO$_3$, extracted with dichloromethane (DCM), and dried over MgSO$_4$. Evaporation of the solvent yielded 31.3 g of an oil which solidified. A portion of this solid (3 g) was dissolved in ethanol (75 ml). Ethanolic HCl was added until the solution was acidic. Ethyl ether (75 ml) was added and the product salt (2.65 g, m.p. 224–225° C. ) precipitated from solution.

Analysis: Calculated for C$_{15}$H$_{18}$ClF$_2$NO: 59.70% C 6.01% H 4.64% N Found: 59.52% C 5.87% H 4.55% N c. Z-(2,4-Difluorophenyl)(8-methyl-8-azabicyclo[3.2.1]octan-3-yl)methanone oxime hydrochloride A mixture of (2,4-difluorophenyl)(8-methyl-8-azabicyclo[3.2.1]octan-3yl)methanone (20 g), hydroxylamine hydrochloride (10.6 g) and ammonium acetate (18.7 g) was heated in 67.5 ml of refluxing ethanol-water (3.2 mixture) for 19 hours. The mixture was concentrated to approximately half of its original volume, and the. precipitated solid (21.3 g) was collected.

d. 3-[6-Fluoro-1,2-benzisoxazol-3-yl]-8-methyl-8-azabicyclo[3.2.1]octane hydrochloride A mixture of (E)-(2,4-difluorophenyl)(8-methyl-8-azabicyclo[3.2.1]octan-3-yl)methanone oxime (18 g), 10% NaOH (36.4 ml) and ethanol (150 ml) was refluxed for 4 hours. The reaction mixture was cooled and concentrated on the rotary evaporator. The mixture was diluted with H$_2$O (500 ml) and extracted with ethyl ether (2×1 L). The ether extract was dried with MgSO₄ and concentrated to yield an oil (13.6 g) which solidified upon standing several hours. A portion of this solid (3.0 g) was dissolved in ethanol and ethanolic HCl was added dropwise until the solution was acidic. 2.1 g of 3-[6-fluoro-1,2-benzisoxazol-3-yl]-8-methyl-8-azabicyclo[3.2.1]octane hydrochloride, m.p. 269°–270° C., precipitated from solution.

Analysis: Calculated for $C_{15}H_{17}FN_2O \cdot HI$: 60.71% C 6.11% H 9.44% N Found: 60.83% C 6.17% H 9.33% N e. 3-(6-Fluoro-1,2-benzisoxazol-3-yl)-8-azabicyclo[3.2.1]octane hydrochloride Vinyl chloroformate (2.9 g) was added dropwise to a solution of 3-(6-fluoro-1,2-benzisoxazol-3-yl)-8-methyl-8-azabicyclo[3.2.1]octane (5.6 g) and potassium carbonate (3.6 g) in 125 ml of 1,2-dichloroethane at 0° C. The resulting suspension was heated at reflux for 3 hours, the solution was cooled, and the solvent was removed in vacuo. The residue was suspended in 125 mL of ethanol and acidified with HCl in ethanol (to about a pH of 1), and the mixture was heated at reflux for 2 hours. The mixture was cooled, and 3.6 g of 3-(6-fluoro-1,2-benzisoxazol-3-yl)-8-azabicyclo[3.2.1]octane hydrochloride, m.p. 248°–250° C., crystallized out of solution.

Analysis: Calculated for $C_{14}H_{16}ClFN_2O$: 59.46% C 5.71% H 9.91% N Found: 59.59% C 5.73% H 9.83% N f. [4-[3-[3-[6-Fluoro-1,2-benzisoxazol-3-yl]-8-azabicyclo[3.2.1]octan-8-yl]-3-methoxyphenyl]ethanone hydrochloride A mixture of 3-[6-fluoro-1,2-benzisoxazol-3-yl]-8-azabicyclo[3.2.1]octane (3.3 g), $K_2CO_3$ (2.21 g), 4-(3-chloropropoxy)-3-methoxyphenyl ethanone (3.9 g) and acetonitrile (150 ml) was stirred and refluxed for 18 hours. The mixture was filtered and the filtrate was evaporated under reduced pressure. The residue was purified using Prep 500 chromatography (5% methanol/1% triethylamine/94% DCM) to yield 3.4 g of an oil. The oil was dissolved in ethanol (40 ml) and ethanolic HCl was added until the solution was acidic. Ethyl ether (approximately 100 ml) was added and 2.4 g of [4-[3-[3-[6-fluro-1,2-benzisoxazol-3-yl]-8-azabicyclo[3.2.1]octan-8-yl]propoxy]-3-methoxyphenyl]ethanone hydrochloride precipitated from solution as a solid, m.p. 219°–220° C.

Analysis: Calculated for $C_{26}H_{30}ClFN_2O_4$: 63.86% C 6.18% H 5.73% N Found: 63.69% C 6.09% H 5.60% N

EXAMPLE 3

[4-[3-[3-[1,2-Benzisoxazol-3-yl]-8-azabicyclo[3.2.1]octan-8-yl]propoxy]-3-methoxyphenyl] ethanone fumarate A mixture of 3-(1,2-benzisoxazol-3-yl)-8-azabicyclo[3.2.1]octane (3.2. g), 4-(3-chloropropoxy)-3-methoxyphenylphenyl ethanone (4.0 g), potassium carbonate (3.9 g) and a catalytic amount of potassium iodide was heated in 60 ml of refluxing acetonitrile for 19 hours. The resulting mixture was allowed to cool to room temperature, diluted with water and extracted into dichloromethane. The organic layer was washed with brine, dried with MgSO₄, filtered, and concentrated to give 7.1 g of an oil, which was dissolved in diethyl ether and acidified with HCl in isopropanol. The solid was collected by filtration, suspended in water, and basified with 10% NaOH solution. The product was extracted into dichloromethane, and then washed sequentially with water and brine, dried over $K_2CO_3$, filtered, and concentrated to provide 4.0 g of crude product. Purification by HPLC on silica gel (elution with ethyl acetate) afforded 2.7 g of product as an oil. The oil (2.5 g) was dissolved in hot ethanol, and it was treated with an equivalent amount of fumaric acid. Isopropyl ether was added to the solution, and the fumarate was allowed to crystallize. Filtration gave 2.85 g of [4-[3-[3-[1,2-benzisoxazol-3-yl]-8-azabicyclo[3.2.1]octan-8-yl]propoxy]-3-methoxyphenyl] ethanone fumarate, m.p. 176°–178° C.

Analysis: Calculated for $C_{30}H_{34}N_2O_8$: 65.44% C 6.22% H 5.09% N Found: 65.11% C 6.25% H 5.06% N

EXAMPLE 4

[4-[2-[3-[6-Fluoro-1,2-benzisoxazol-3-yl]-8-azabicyclo[3.2.1]octan-8-yl]ethoxy]-3-methoxyphenyl] ethanone fumarate A mixture of 3-(6-fluoro-1,2-benzisoxazol-3-yl)-8-azabicyclo[3.2.1]octane (3.0 g), 4-(2-chloroethoxy)-3-methoxyphenyl ethanone (3.6 g), and potassium carbonate (2.2 g), was heated in 200 ml of refluxing acetonitrile for 22 hours. The resulting mixture was allowed to cool to room temperature and filtered. The filtrate was concentrated and purified by HPLC on silica gel (elution with triethylamine-methanol-ethyl acetate) to afford 2.6 g of product as an oil. The oil was dissolved in methanol, and fumaric acid (0.76 g) was added. The product crystallized from solution upon addition of ethyl ether to afford 2.0 g of [4-[2-[3-[6-fluoro-1,2-benzisoxazol-3-yl]-8-azabicyclo[3.2.1]octan-8-yl]ethoxy]-3-methoxyphenyl]ethanone fumarate, as a powder, m.p. 171°–172° C.

Analysis: Calculated for $C_{29}H_{31}FN_2O_8$: 62.81% C 5.63% H 5.05% N Found: 62.69% C 5.61% H 5.02% N

EXAMPLE 5

[4-[2-[3-[1,2-Benzisoxazol-3-yl]-8-azabicyclo[3.2.1]octan-8-yl]ethoxy]-3-methoxyphenyl] ethanone fumarate A mixture of 3-(1,2-benzisoxazol-3-yl)-8-azabicyclo[3.2.1]octane (3.4 g), 4-(2-chloroethoxy)-3-methoxyphenyl ethanone (4.1 g), potassium carbonate (4.1 g) and a catalytic amount of potassium iodide was heated in 60 ml of refluxing acetonitrile for 19 hours. The resulting mixture was allowed to cool to room temperature and then was filtered. The filtrate was concentrated, and the residue was dissolved in diethyl ether and acidified with HCl in isopropanol. The solid was collected by filtration, suspended in water, and basified with 10% NaOH solution. The product was extracted into dichloromethane, and then washed sequentially with water and brine, dried over $K_2CO_3$, filtered, and concentrated to provide 4.7 g of crude product. Purification by HPLC on silica gel (elution with ethyl acetate) afforded 2.8 g of product as an oil. The oil (2.55 g) was dissolved in hot ethanol, and the solution was treated with an equivalent amount of fumaric acid. Isopropyl ether was added to the solution, and the fumarate was allowed to crystallize. Filtration gave 2.95 g of [4-[2-[3-[1,2-benzisoxazol-3-yl]-8-azabicyclo[3.2.1]octan-8-yl]ethoxy]-3-methoxyphenyl] ethanone fumarate, m.p. 182°–183.5° C.

Analysis: Calculated for $C_{29}H_{32}N_2O_8$: 64.91% C 6.01% H 5.22% N Found: 64.92% C 6.02% H 5.20% N

EXAMPLE 6

[4-[4-[3-[6-Fluoro-1,2-benzisoxazol-3-yl]-8-azabicyclo[3.2.1]octan-8-yl]butoxy]-3-methoxyphenyl] ethanone fumarate A mixture of 3-(6-fluoro-1,2-benzisoxazol-3-yl)-8-azabicyclo[3.2.1]octane (3.5 g), 4-(4-bromobutoxy)-3-methoxyphenyl ethanone (5.1 g), and potassium carbonate (2.4 g) was heated in 200 ml of refluxing acetonitrile for 22 hours. The resulting mixture was allowed to cool to room temperature and filtered. The filtrate was concentrated and purified by HPLC on silica gel (elution with triethylamine- methanol- ethyl acetate) to afford 5.3 g of product as an oil. The oil was dissolved in methanol and fumaric acid (1.4 g) was added. The product crystallized upon addition of ethyl ether affording 4.2 g of [4-[4-[3-[6-fluoro-1,2-benzisoxazol-3-yl]-8-azabicyclo[3.2.1]octan-8-yl]butoxy]-3-methoxyphenyl] ethanone fumarate, as a powder, m.p. 139°–141° C.

Analysis: Calculated for $C_{31}H_{35}FN_2O_8$: 63.90% C 6.07% H 4.81% N Found: 63.68% C 5.95% H 4.69% N

EXAMPLE 7 a. 3-(1H-Indazol-3-yl)-8-methyl-8-azabicyclo[3.2.1]octane

A mixture of (2-fluorophenyl) (8-methyl-8-azabicyclo-[3.2.1]octan-3-yl) methanone (24.6 g), hydrazine hydrate (14.4 ml), and ethanol (250 ml) was heated to reflux for four hours. The reaction was cooled to room temperature and concentrated to an oil. This residue was dissolved in dimethylformamide (DMF) (250 ml). Potassium carbonate (28 g) was added to the mixture which was subsequently heated at reflux for 2 days. The reaction mixture was cooled and filtered and the DMF was removed in vacuo. residue was dissolved in ethanol and 5.2 g of 3-(1H-indazol-3-yl)-8-methyl-8-azabicyclo[3.2.1]octane precipitated from solution, as a powder, m.p. 191°–192° C.

Analysis: Calculated for $C_{15}H_{19}N_3$: 74.64% C 7.95% H 17.41% N
74.53%C 8.02%H 17.21%N Found: 74.53% C 8.02% H 17.21% N 8-Cyano-3-(1H-indazol-3-yl)-8-azabicyclo[3.2.1]octane Cyanogen bromide (10 g) was added in one portion to a suspension of (1H-indazol-3-yl)-8-methyl-8-azabicyclo[3.2.1]octane (11 g) and potassium carbonate (12 g) in dimethylformamide (250 ml) at room temperature. The mixture was stirred for 3 hours after which it was diluted with water, and extracted with ethyl acetate (3×300 ml). The combined organic solution was washed with brine, dried over $MgSO_4$, filtered and concentrated to leave 11 g of an oil. Crystallization from DCM:hexane provided 3.1 gm of a solid, m.p. 199°–201° C. Recrystallization from ethanol gave 1.15 g of crystals, m.p. 201°–202° C.

Analysis: Calculated for $C_{15}H_{16}N_4$: 71.40% C 6.39% H 22.20% N Found: 71.09% C 6.29% H 22.03% N c. 3-(1H-Indazol-3-yl)-8-azabicyclo[3.2.1]octane fumarate hemihydrate To 8-cyano-3-(1H-indazol-3-yl)-8-azabicyclo[3.2.1]octane (2.1 g) in THF (50 ml) was added lithium aluminum hydride (1.26 g) in portions under $N_2$ at 0° C. The mixture was heated at reflux for 2 hours, cooled to room temperature, quenched water, diluted with ethyl acetate then followed with 20 ml of 10% NaOH. The precipitates were filtered and the solution was concentrated to dryness. The crude residue was dissolved into ethanol and filtered again. The ethanol solution was treated with a solution of fumaric acid (1.18 g) to yield 2.82 g of a solid. The solid was collected and recrystallized twice from ethanol to give 1.51 g of crystals, m.p. 218°–219° C.

Analysis: Calculated for $C_{14}H_{17}N_3 \cdot C_4H_4O_4 \cdot 0.5H_2O$: 61.37% C 6.29% H 11.92% N Found: 61.62% C 6.51% H 11.74% N d. [4-[3-[3-[1H-Indazol-3-yl]-8-azabicyclo[3.2.1]octan-8-yl]propoxy]-3-methoxyphenyl] ethanone A mixture of 3-(1H-indazol-3-yl)-8-azabicyclo[3.2.1]octane (5.46 g), 4-(3-chloropropoxy)-3-methoxyphenyl ethanone (6.4 g), potassium carbonate (6.6 g) and a catalytic amount of potassium iodide was heated in 100 ml of refluxing acetonitrile for 17 hours. The resulting mixture was allowed to cool to room temperature and filtered. The filtrate was concentrated, and the residue was dissolved in 6N HCl solution and extracted with ethyl acetate. The aqueous layer was basified with 10% NaOH solution, and the product was extracted into dichloromethane. The combined organic layers were washed with brine, dried over $K_2CO_3$, filtered, and concentrated to provide 7.0 g of a foam. Purification by HPLC on silica gel (elution initially with ethyl acetate, and then 10% methanol-90% ethyl acetate) afforded 4.2 g of product as a foam. The foam crystallized upon the addition of ethyl acetate, and the solid was then recrystallized from ethyl acetate-hexanes, affording 2.8 g of [4-[3-[3-[1H-indazol-3-yl]-8-azabicyclo[3.2.1]octan-8-yl]propoxy]-3-methoxyphenyl] ethanone, as a powder, m.p. 173°–175° C.

Analysis: Calculated for $C_{26}H_{31}N_3O_3$: 72.03% C 7.21% H 9.69% N Found: 71.69% C 7.14% H 9.64% N

EXAMPLE 8

[4-[2-[3-[1H-Indazol-3-yl]-8-azabicyclo[3.2.1]octan-8-yl]-ethoxy]-3-methoxynhenyl] ethanone A mixture of 3-(1H-indazol-3-yl)-8-azabicyclo[3.2.1]octane (4.1 g), 4-(2-chloroethoxy)-3-methoxyphenyl ethanone (5.9 g) and potassium carbonate (2.7 g) was heated in 125 ml of refluxing acetonitrile for 22 hours. The resulting mixture was allowed to cool to room temperature and then filtered. The filtrate was concentrated and purified by HPLC on silica gel (elution with triethylamine- methanol- ethyl acetate) to afford 2.3 g of product as an oil. The oil was dissolved in ethyl acetate and the product crystallized affording 1.6 g of [4-[2-[3-[1H-indazol-3-yl]-8-azabicyclo[3.2.1]octan-8-yl]ethoxy]-3-methoxyphenyl] ethanone, as a powder, m.p. 154°–155° C.

Analysis: Calculated for $C_{25}H_{29}N_3O_3$: 71.56% C 6.98% H 10.02% N Found: 71.42% C 6.95% H 9.98% N

EXAMPLE 9

[4-[4-[3-[1H-Indazol-3-yl]-8-azabicyclo[3.2.1]octan-8-yl]butoxy]-3-methoxyphenyl] ethanone fumarate hemihydrate A mixture of 3-(1H-indazol-3-yl)-8-azabicyclo[3.2.1]octane (3.1 g), 4-(4-brmobutoxy)-3-methoxyphenyl ethanone (4.52 g) and potassium carbonate (3.7 g) was heated in 56 ml of refluxing acetonitrile for 22 hours. The resulting mixture was allowed to cool to room temperature and then filtered. The filtrate was diluted with dichloromethane, and then washed sequentially with water and brine, dried over $K_2CO_3$, filtered, and concentrated to provide 6.0 g of crude product. Purification by HPLC on silica gel (elution with triethylamine-methanol-ethyl acetate) afforded 3.4 g of product as an oil. The oil was dissolved in ethanol, and the solution was treated with an equivalent amount of fumaric acid. The solvent was removed in vacuo, and the resulting foam was crystallized from water, affording 3.3 g of [4-[4-[3-[1H-indazol-3-yl]-8-azabicyclo[3.2.1]octan-8-yl]butoxy]-3-methoxyphenyl] ethanone fumarate hemihydrate, as a powder, m.p. 170°-173° C.

Analysis: Calculated for $C_{31}H_{37}N_3O_7 \cdot 0.5H_2O$: 65.02% C 6.69% H 7.34% N Found: 65.08% C 6.74% H 7.22% N

EXAMPLE 10 a. 3-(6-Fluoro-1H-indazol-3-yl)-8-methyl-8-azabicyclo[3.2.1]octane

A mixture of (2,4-difluorophenyl)(8-methyl-8-azabicyclo-[3.2.1]octan-3-yl)methanone (25.5 g), hydrazine hydrate (21 g) and ethanol (250 ml) was heated at reflux for 16 hours. The reaction mixture was concentrated to an oil on the rotary evaporator. The residue was dissolved in DMF (350 ml) and potassium carbonate (25 g) was added to the mixture which was refluxed for 16 hours. The mixture was cooled, filtered and stripped down in vacuo. The residue was dissolved in hot ethanol to yield 4.96 g of a solid. Recrystallization from ethanol gave 3.88 g of crystals, m.p. 235°-236° C.

Analysis: Calculated for $C_{15}H_{18}FN_3$: 69.47% C 7.00% H 16.20% N Found: 69.52% C 7.06% H 16.19% N b. 8-Cyano-3-(6-fluoro-1H-indazol-3-yl)-8-azabicyclo-[3.2.1]octane Cyanogen bromide (2.75 g) was added in one portion to a suspension of 3-(6-fluoro-1H-indazol-3-yl)-8-methyl-8-azabicyclo[3.2.1]octane (4.90 g) and potassium carbonate (2.75 g) in 70 ml of THF at room temperature. The mixture was stirred for 2 hours, then diluted with water and the product was extracted into ethyl acetate. The organic solution was washed with brine, dried over MgSO4, filtered and concentrated to leave 3.4 g of crude solids. The solids were purified by flash chromatography over silica gel and recrystallized from ethanol to yield 1.15 g of the desired product, m.p. 182°-184° C.

c. 3-(6-Fluoro-1H-indazol-3-yl)-8-azabicyclo[3.2.1]-octane hydrochloride

A solution of 8-cyano-3-(6-fluoro-1H-indazol-3-yl)-8-azabicyclo[3.2.1]octane (9.8 g) in THF (200 ml) was treated with lithium aluminum hydride (65 ml, 1M in THF) dropwise at 0° C. under $N_2$. The resulting mixture was heated at reflux for 4 hours and then cooled to 0° C. Ice chips were added to quench the excess reagent. The mixture was with ethyl acetate (100 ml), then there was added 20% NaOH (10 ml) and $H_2O$ (10 ml). The insolubles were filtered and the organic solution was dried over MgSO4 and concentrated to a foam (8.36 g). The foam was dissolved into ethanol, treated with HCl in ethanol (50 ml) and stirred overnight to yield 1.43 g of crystals, m.p. 285°-295° C. (dec).

Analysis: Calculated for $C_{14}H_{16}FN_3 \cdot HCl$: 59.68% C 6.08% H 14.91% N 59.08% C 6.28% H 14.55% N d. [4-[2-[3-6-Fluoro-1H-indazol-3-yl]-8-azabicyclo-[3.2.1]octan-8-yl]ethoxy]-3-methoxyphenyl] ethanone A mixture of 3-(6-fluoro-1H-indazol-3-yl)-8-azabicyclo[3.2.1]octane (3.8 g), 4-(2-chloroethoxy)-3-methoxyphenyl ethanone (4.8 g) and potassium carbonate (4.8 g) was heated in 125 ml of refluxing acetonitrile for 22 hours. The resulting mixture was allowed to cool to room temperature and then filtered. The filtrate was concentrated and purified by HPLC on silica gel (elution with triethylamine-methanol-ethyl acetate) to afford 3.8 g of product as an oil. The oil was dissolved in isopropyl alcohol (IPA) and the product crystallized affording 2.1 g of [4-[2-[3-[6-fluoro-1H-indazol-3-yl]-8--azabicyclo[3.2.1]octan-8-yl]ethoxy]-3-methoxyphenyl] ethanone, as a powder, m.p. 151°-152° C.

Analysis: Calculated for $C_{25}H_{28}FN_3O_3$: 68.63% C 6.45% H 9.60% N Found: 68.48% C 6.45% H 9.51% N

EXAMPLE 11

[4-[4-[3-[6-Fluoro-1H-indazol-3-yl]-1-8-azabicyclo[3.2.1]-octan-8-yl]butoxy]-3-methoxynhenyl] ethanone A mixture of 3-(6-fluoro-1H-indazol-3-yl)-8-azabicyclo[3.2.1]octane (6.0 g), 4-(4-bromobutoxy)-3-methoxyphenyl ethanone (7.5 g) and potassium carbonate (6.7 g) was heated in 150 ml of refluxing acetonitrile for 22 hours. The resulting mixture was allowed to cool to room temperature and then filtered. The filtrate was concentrated and purified by HPLC on silica gel (elution with triethylamine-methanol-ethyl acetate) to afford 4.6 g of product as an oil. The oil was dissolved in isopropyl alcohol, and the product crystallized affording 2.2 g of [4-[4-[3-[6-fluoro-1H-indazol-3-yl]-8-azabicyclo[3.2.1]octan-8-yl]butoxy]-3-methoxyphenyl] ethanone, as a powder, m.p.148°-149° C.

Analysis: Calculated for $C_{27}H_{32}FN_3O_3$: 69.66% C 6.93% H 9.03% N Found: 69.52% C 7.09% H 8.99% N

EXAMPLE 12

[4-[3-[3-[6-Fluoro-1H-indazol-3-yl]-8-azabicyclo[3.2.1]-octan-8-yl]propoxy]-3-methoxyphenyl] ethanone A mixture of 3-(6-fluoro-1H-indazol-3-yl)-8-azabicyclo[3.2.1]octane (4.3 g), 4-(3-chloropropoxy)-3-methoxyphenyl ethanone (4.7 g) and potassium carbonate (2.8 g) was heated in 150 ml of refluxing acetonitrile for 18 hours. The resulting mixture was allowed to cool to room temperature and then filtered. The filtrate was concentrated, and the residue was dissolved in $H_2O$ and extracted with 4:1 $CHCl_3$/IPA. The combined organic layers were dried over $Mg_2SO_4$, filtered and concentrated. Purification by HPLC on silica gel (elution initially with ethyl acetate, and then with 10% methanol-89% ethyl acetate-1% TEA) afforded 3.1 g of product as a foam. The foam was dissolved in methanol (50 ml) and the product crystallized affording 2.8 g of [4-[3-[3-[6-fluoro-1H-indazol-3-yl]-8-azabicyclo[3.2.1]octan-8-yl]propoxy]-3-methoxyphenyl] ethanone, as a solid m.p. 157°-158° C.

Analysis: Calculated for $C_{26}H_{30}FN_3O_3$: 69.14% C 6.71% H 9.31% N Found: 68.97% C 6.99% H 9.31% N

EXAMPLE 13 a. 3-[1,2-Benzisothiazol-3-yl]-8-methyl-8-azabicyclo[3.2.1]octane hydrochloride

A mixture of (2-fluorophenyl)(8-methyl-8-azabicyclo-[3.2.1]octan-3-yl)methanone (20 g) and sulphur (3.2 g) in a saturated solution of $NH_3$ in 2-methoxyethanol (240 ml) was stirred in an autoclave at 160° C. for 2 hours, and then cooled. The reaction mixture was poured into $H_2O$ (250 ml), extracted with DCM, and the organic phase was concentrated to an oil. This residue was purified by HPLC on silica gel (ethyl acetate/methanol/triethylamine) to yield an oil (6.3 g) which solidified upon standing. The solid (2.0 g) was dissolved in methanol. Ethereal HCl was added until the solution was acidic. Upon addition of ethyl ether, the product salt (1.7 g) precipitated from solution. Recrystallization twice from methanol yielded 0.5 g of 3-[1,2-benzisothiazol-3-yl]-8-methyl-8-azabicyclo[3.2.1]octane hydrochloride, m.p. 271°–273° C.

Analysis: Calculated for $C_{15}H_{19}ClN_2S$: 61.09% C 6.51% H 9.50% N Found: 60.87% C 6.49% H 9.38% N b. 3-(1,2-Benzisothiazol-3-yl)-8-azabicyclo[3.2.1]octane Vinyl chloroformate (4.4 g) was added dropwise to a solution of carbonate (4.76 g) in 250 ml of 1,2-dichloroethane. The resulting suspension was heated reflux for 3 hours, and then the solution was cooled, and the solvent was removed in vacuo. The residue was suspended in isopropyl alcohol and acidified with HCl in isopropanol (to about a pH of 1 ), and the mixture was heated at reflux for 1 hour. The mixture was cooled, made basic, and then the product was extracted into dichloromethane. The combined organic layers were dried over $MgSO_4$, filtered and concentrated to provide 8.5 g of 3-(1,2-benzisothiazol-3-yl)-8-azabicyclo[3.2.1]octane which was used subsequently without purification.

c. [4-[2-[3-[1,2-Benzisothiazol-3-yl]-8azabicyclo[3.2.1]-octan-8-yl]ethoxy-3-methoxyphenyl] ethanone fumarate A mixture of 3-(1,2-benzisothiazol- 3-yl)-8-azabicyclo[3.2.1]octane (4.8 g), 4-(2-chloroethoxy)-3-methoxyphenyl ethanone (5.8 g) and potassium carbonate (3.5 g) was heated in 250 ml of refluxing acetonitrile for 22 hours. The resulting mixture was allowed to cool to room temperature and then filtered. The filtrate was concentrated and purified by HPLC on silica gel (elution with triethylamine-methanol-ethyl acetate) to afford 2.8 g of product as an oil. The oil was dissolved in ethanol and fumaric acid (0.82 g dissolved in ethanol) and was added to the free base in solution. The product (1.2 g) precipitated from solution upon addition of ethyl ether. The mother liquor was stripped of solvent, basified with NaOH and extracted with DCM. This crude free base was further purified by HPLC on silica gel to yield 1.2 g of an oil. The fumarate was prepared as before and was recrystallized from methanol to yield 0.8 g of the salt. The product samples were combined to yield 1.9 g of [4-[2-[3-[1,2-benzisothiazol-3-yl]-8azabicyclo]3.2.1]octan-8-yl]ethoxy]-3-methoxyphenyl] ethanone fumarate, as a solid, m.p. 157°–158° C.

Analysis: Calculated for $C_{29}H_{32}N_2O_7S$: 63.03% C 5.84% H 5.07% N Found: 62.95% C 5.78% H 5.00% N

EXAMPLE 14

[4-[3-[3-[1,2-Benzisothiazol-3-yl]-8-azabicyclo[3.2.1]-octan-8-yl]propoxy]-3-methoxyphenyl] ethanone fumarate A mixture of 3-( 1,2-benzisothiazol-3-yl)-8-azabicyclo[3.2.1]octane (2.8 g), 4-(3-chloropropoxy)-3-methoxyphenyl ethanone (3.1 g), and potassium carbonate (1.8 g) was heated in 150 ml of refluxing acetonitrile for 22 hours. The resulting mixture was allowed to cool to room temperature and then filtered. The filtrate was concentrated and purified by HPLC on silica gel (elution with triethylamine- methanol- ethyl acetate) to afford 3.8 g of product as an oil. The oil was dissolved in methanol and fumaric acid (1.1 g dissolved in methanol) and was added to the free base in solution. The product (4.0 g) precipitated from solution upon addition of ethyl ether. This product was then recrystallized from methanol to yield 2.8 g of [4-[3-[3-[1,2-benzisothiazol-3-yl]-8-azabicyclo[3.2.1 ]octan-8-yl]propoxy]-3-methoxyphenyl] ethanone fumarate, m.p. 159°–160° C.

Analysis: Calculated for $C_{30}H_{34}N_2O_7S$: 63.59% C 6.05% H 4.94% N Found: 63.83% C 6.00% H 5.00% N

EXAMPLE 15

[4-[4-[3-[1,2-Benzisothiazol-3-yl]-8-azabicyclo[3.2.1]-octan-8-yl]butoxy]-3-methoxyphenyl] ethanone hydrochloride A mixture of 3-(1,2-benzisothiazol-3-yl)-8-azabicyclo[3.2.1]octane (3.6 g), 4-(4-bromobutoxy)-3-methoxyphenyl ethanone (5.3 g) and potassium carbonate (2.5 g) was heated in 150 ml of refluxing acetonitrile for 22 hours. The resulting mixture was allowed to cool to room temperature and then filtered. The filtrate was concentrated and purified by HPLC on silica gel (elution with triethylamine-methanol-ethyl acetate) to afford 5.4 g of product as an oil. The oil was dissolved in methanol and ethereal HCl was added dropwise until the pH was acidic. The product crystallized from solution upon addition of additional ethyl ether affording 3.2 g of a powder. This product was then recrystallized from methanol to yield 2.1 g of [4-[4-[3-[1,2-benzisothiazol-3-yl]-8-azabicyclo[3.2.1]octan-8-yl]butoxy]-3-methoxyphenyl] ethanone hydrochloride, m.p. 205°–206° C.

Analysis: Calculated for $C_{27}H_{33}ClN_2O_3S$: 64.70% C 6.65% H 5.59% N Found: 64.45% C 6.63% H 5.49% N

EXAMPLE 16

3-[6-Fluoro-1,2-benzisothiazol-3-yl]-8-azabicyclo-[3.2.1]octane fumarate

A slurry of 8-cyano-3-[6-fluoro-1,2-benzisothiazol-3-yl]-8-azabicyclo[3.2.1]octane in 10% hydrochloric acid was refluxed for 6 hours. The mixture was cooled in an ice bath and was basified with 10% NaOH. The product was extracted into dichloromethane. The organic layer was dried over anhydrous magnesium sulfate ($MgSO_4$), filtered and concentrated to yield 5.2 g of the product as an oil which solidified upon standing. This solid (2.2 g) was purified via Prep 500 chromatography to yield a solid (1.8 g) which was dissolved in methanol. Fumaric acid (1.1 eq. dissolved in methanol) was added and the solution was concentrated to approximately 30 ml. The analytically pure material (m.p. 228°–229° C.) crystallized from solution upon standing overnight.

Analysis: Calculated for $C_{18}H_{19}FN_2O_4S$: 57.13% C 5.06% H 7.40% N Found: 57.03% C 5.07% H 7.28% N

EXAMPLE 17

[4-[3-[3-[6-Fluoro-1,2-benzisothiazol-3-yl]-8-azabicyclo[3.2.1]octan-8-yl]propoxy]-3-methoxyphenyl] ethanone A mixture of 3-(6-fluoro-1,2-benzisothiazol-3-yl)-8-azabicyclo[3.2.1 ]octane (3.0 g), 4-(3-chloropropoxy)-3-methoxyphenyl ethanone (3.5 g) and potassium carbonate (1.9 g) was heated in 100 ml of refluxing acetonitrile for 22 hours. The resulting mixture was allowed to cool to room temperature and filtered. The filtrate was concentrated and purified by HPLC on silica gel (elution with triethylamine-methanol-ethyl acetate) to afford 3.3 g of product as an oil. The oil was dissolved in methanol (approximately 10 ml) and crystallized slowly from solution to yield 2.75 g of [4-[3-[3-[6-fluoro-1,2-benzisothiazol-3-yl]-8-azabicyclo[3.2.1]octan-8-yl]propoxy]-3-methoxyphenyl] ethanone, m.p. 118°–119° C.

Analysis: Calculated for $C_{26}H_{29}FN_2O_3S$: 66.63% C 6.25% H 5.98% N Found: 66.70% C 6.24% H 5.85% N

We claim:

1. A compount which is (2-fluorophenyl)(8-methyl-8-azabicyclo[3.2.1]octan-3-yl) methanone or a pharmaceutically acceptable acid addition salt thereof.

2. A compound which is (2,4-difluorophenyl)(8-methyl-8-azabicyclo[3.2.1]octan-3-yl) methanone or a pharmaceutically acceptable acid addition salt thereof.

3. A compound which is (2-fluorophenyl)(8-methyl-8-azabicyclo[3.2.1]octan-3-yl) methanone oxime.

4. A compound which is (2,4-difluorophenyl)(8-methyl-8-azabicyclo[3.2.1]octan-3-yl)m ethanone oxime or a pharmaceutically acceptable acid addition salt thereof.

* * * * *